United States Patent [19]
Urbanczyk

[11] Patent Number: 5,818,570
[45] Date of Patent: Oct. 6, 1998

[54] DEVICE AND METHOD FOR RECORDING OR TRANSFERRING GRAPHICAL INFORMATION FOR ANALYSIS AND STORAGE PURPOSES

[76] Inventor: Matthias Urbanczyk, Königin-Elisabeth-Str. 58, D-1000 Berlin 19, Germany

[21] Appl. No.: 516,020

[22] Filed: Aug. 16, 1995

Related U.S. Application Data

[63] Continuation-in-part of Ser. No. 67,839, May 27, 1993, abandoned.

[30] Foreign Application Priority Data

May 29, 1992 [DE] Germany ............................ 42 18 337.5

[51] Int. Cl.⁶ ............................ G03B 27/02; G03B 27/52; G03B 27/62
[52] U.S. Cl. .................................. 355/75; 355/40; 355/79
[58] Field of Search ................................ 355/75, 78, 79, 355/39, 40, 77; 33/1; 353/44, 45, 87; 434/87–90

[56] References Cited

U.S. PATENT DOCUMENTS

3,913,118  10/1975  Abrams ...................... 355/79
4,241,994  12/1980  Ryan ......................... 355/40 X
4,328,051   5/1982  Robinette .................... 156/62
4,368,587   1/1983  Childs ....................... 355/79 X
4,550,502  11/1985  Grayzel ...................... 33/1 B
4,975,735  12/1990  Bright et al. ................ 355/77 X
5,409,383   4/1995  Mannino ...................... 434/414

*Primary Examiner*—Fred L. Braun
*Attorney, Agent, or Firm*—Schlesinger Arkwright & Garvey LLP

[57] ABSTRACT

A device for recording or transferring graphical information from a sample medium for analysis and storage purposes includes a generally planar, transparent base which overlies the sample with the information to be recorded. A generally transparent recording medium overlies the base and is provided with indicia. By comparing the indicia with the information recorded on the recording medium, an analysis can be made. At least a part of the indicia may be used to form an anti-tampering arrangement which prevents unauthorized tampering of the information stored on the recording medium. A method of recording graphical information representing medical data for analysis and storage purposes is also part of the invention.

15 Claims, 13 Drawing Sheets

FIG. 11 ated with magnetic storage media. Rather, the present invention uses a storage medium which includes at least one layer of substantially transparent material that can be marked for recording graphical information.

DEVICE AND METHOD FOR RECORDING OR TRANSFERRING GRAPHICAL INFORMATION FOR ANALYSIS AND STORAGE PURPOSES

This application is a continuation-in-part of U.S. Ser. No. 08/067,839, filed on May 27, 1993, now abandoned.

FIELD OF THE INVENTION

The invention relates to a device and a method for evaluating, recording or transferring graphical information from, for example, the hardcopy results of an electrocardiogram (ECG) or the like, to a two-dimensional medium for further analysis and storage.

DESCRIPTION OF PRIOR ART

Medical data, for example, the hardcopy results of an electrocardiogram (ECG) or the like, is typically obtained by a medical professional subsequent to a cardiac condition of a patient. It is very desirable to analyze, store, process or compare such data in order to observe or monitor the progress of cardiac condition or otherwise and to formulate and effectuate an adequate plan for treatment or therapy. Since the ECG results are in the form of a continuous paper or the like web, it is often difficult to compare the results of ECG's taken at different times. It is therefore conventional to digitize the ECG results by means of a digitizer connected to a computer. It is also conventional to evaluate and to compare scientific results by at least two analyzing persons separately. The digitized data is then processed by the computer in order to perform the desired tasks.

One can appreciate that not only is this process time consuming, requires computer-related knowledge and often difficult, the equipment necessary to perform the digitization and the processing of the information is expensive. It is necessary, when manually digitizing graphical data to read into the computer dot after dot, a sequence of dots (for instance following a continuous curve), to move a cursor or a digitizing stylus over the paper or like web containing the graphical information. It is difficult to determine the accurate course of the curve during the digitizing process since there can be a considerable amount of superpositions and discontinuities due to the fact that the curve to be digitized stems from a biological process and therefore lacks mathematical rigor and is not a well-defined line. It is also difficult to reproduce this process to evaluate the same parameter (data) configuration.

OBJECTS OF THE INVENTION

It is an object of the invention to provide a device for recording and transferring graphical information for analysis and storage purposes which is easy to use and inexpensive.

It is another object of the invention to provide a device for recording or transferring graphical information using a recording medium which cannot be adversely affected by computer viruses or the like.

It is still another object of the invention to provide a device for recording or transferring graphical information in which the likelihood of unauthorized access or tampering of the graphical information stored on the recording medium is reduced.

It is still another object of the invention to provide a method for recording or transferring graphical information for analysis and storage purposes which is not complicated and allows a quick recording or transferring of graphical information with only a little evaluation time, without the need for special computer-training or knowledge, and which allows to evaluate a lot of single parameters in series, such as intra- and interobserver comparability of serial echocardiographical parameters.

It is still another object of the invention to provide a method for recording or transferring graphical information which allows for simultaneous multiple identical recordings of the information.

Further objects and advantages will become apparent from a consideration of the description in connection with the accompanying drawings.

SUMMARY OF THE INVENTION

The present invention is directed to a device for recording or transferring graphical information from, for example, the hard-copy results of an electrocardiogram (ECG) or the like, to a two-dimensional medium for further analysis and storage. In particular, the device of the present invention includes a generally planar base made of a generally transparent material. A recording medium, also made of a generally transparent material, overlies the base and is detachable therefrom. The recording medium includes anti-tampering mechanism for preventing unauthorized tampering of or access to the data stored on the recording medium.

The invention can be easily understood by having a reference to the results obtained in the form of a tape or the like produced by an ECG machine. It is noted that such medical data is typically obtained by a medical professional subsequent to a cardiac condition of a patient. It is very desirable to analyze, process or compare such data in order to observe or monitor the progress of cardiac condition or otherwise, and to formulate and effectuate an adequate plan for treatment or therapy. Since the ECG results are in form of a continuous paper or the like web, it is often difficult to compare the results of an ECG taken at different times. It is therefore conventional to digitize the ECG results by using a digitizer connected to a computer. The digitized data is then processed by the computer in order to perform the desired task. One can appreciate that not only is this process time consuming, requires computer-related knowledge and often difficult, the equipment necessary to perform the digitization and the processing of the information is expensive. In addition, since the data is typically stored on magnetic storage media, such as discs or tapes, it is susceptible to be adversely affected by computer viruses, magnetic fields or the like. In addition, since the data is stored on magnetic discs or tapes, the likelihood of unauthorized access or tampering remains highly probable.

The present invention is directed to using a storage medium including two layers of substantially transparent material at least one of which can be marked for recording graphical information. The main purpose of the invention is to eliminate the use of conventional storage media, such as magnetic tapes or discs.

BRIEF DESCRIPTION OF THE DRAWINGS

FIG. 5b is a flow chart illustration of the camera unit shown in FIG. 5.

DETAILED DESCRIPTION OF THE INVENTION

Figure 1:
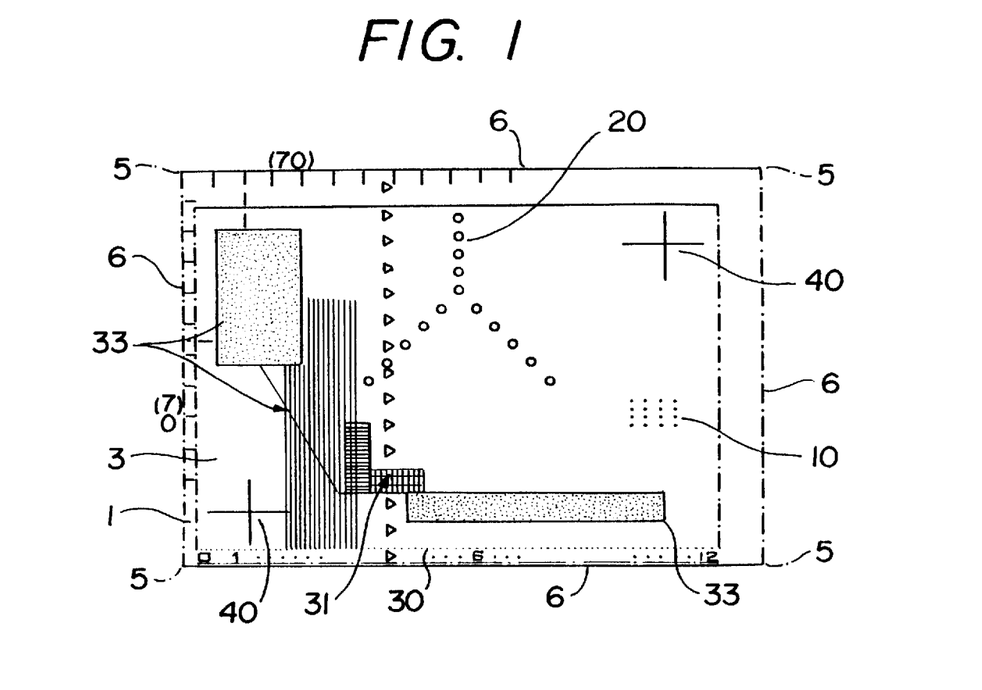
FIG. 1 is a top plan view of a first embodiment of recording medium according to the present invention, including one layer or segment of a transparent material.

FIG. 1 shows a flat rectangular piece of a transparent segment, preferably in the form of a plastic sheet, which according to the invention is used as a recording medium 1 for recording graphical information. The simple plastic sheet comprises a single layer of generally transparent material and may, for example, have the size of a credit card or the like. At least one graphic component 31, shown in sequence at 33, is provided on the layer. In this embodiment, the basic component of the device and at least one single element of the component 31 are shown as a dot matrix 10 for measurement, analysis and code purposes, for example, for determining the distance of image dots relative to each other on a hardcopy containing visual information to be selected, defined and—if necessary or needed—recorded. Furthermore a dot scale 30, which may be used in the same way as matrix 10 or—for instance—two enlarged, single hairline markings 40, which may be used to define the position of the recording and coding means relative to the hardcopy or the objects underneath, behind or beside to be analyzed. Furthermore triple-path segments of markings 20, which also may be used in the same way as matrix 10, are provided on the recording device.

Figure 2:
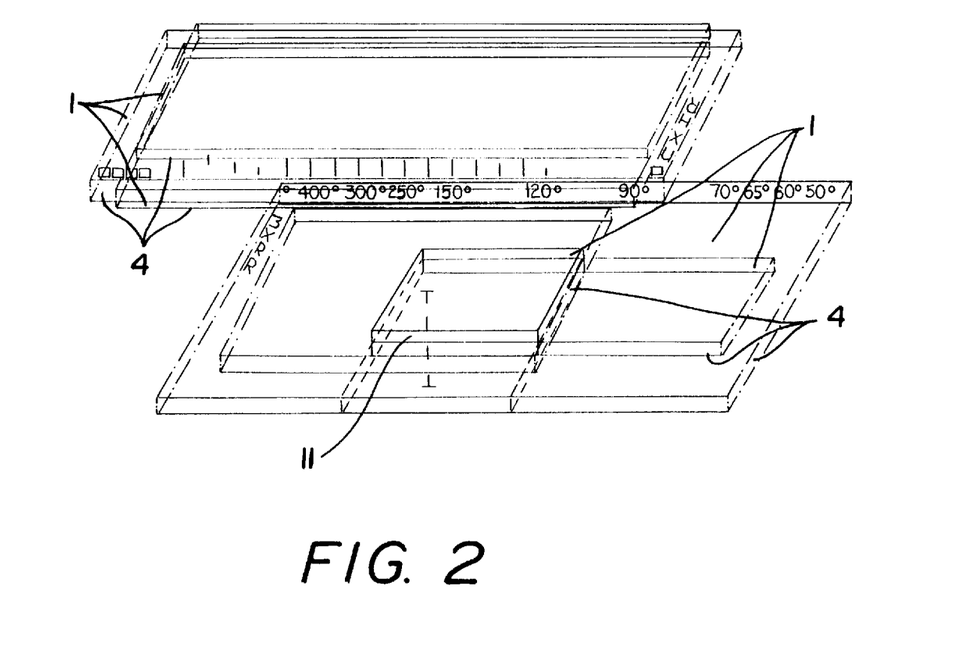
FIG. 2 is a top plan view of another embodiment of the recording medium according to the present invention, including three layers of the transparent material.

FIG. 2 shows another embodiment of a recording medium 1 which consists of three layers 4 of rectangular flat pieces of transparent segments (plastic sheet) differing in size and which is to be separated in parts.

Figure 3:
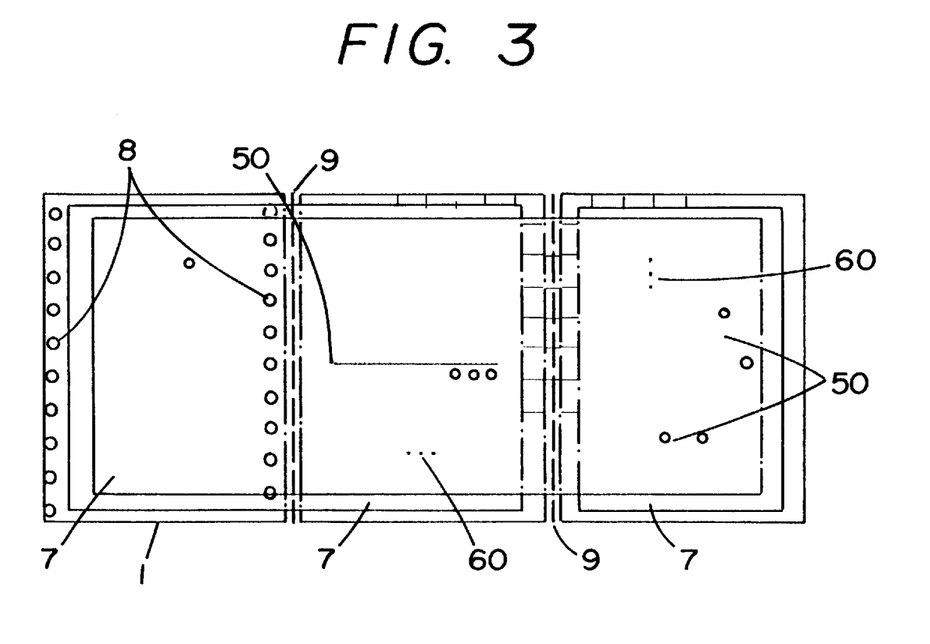
FIG. 3 is a top plan view of another embodiment of a foldable recording medium.
Figure 4:
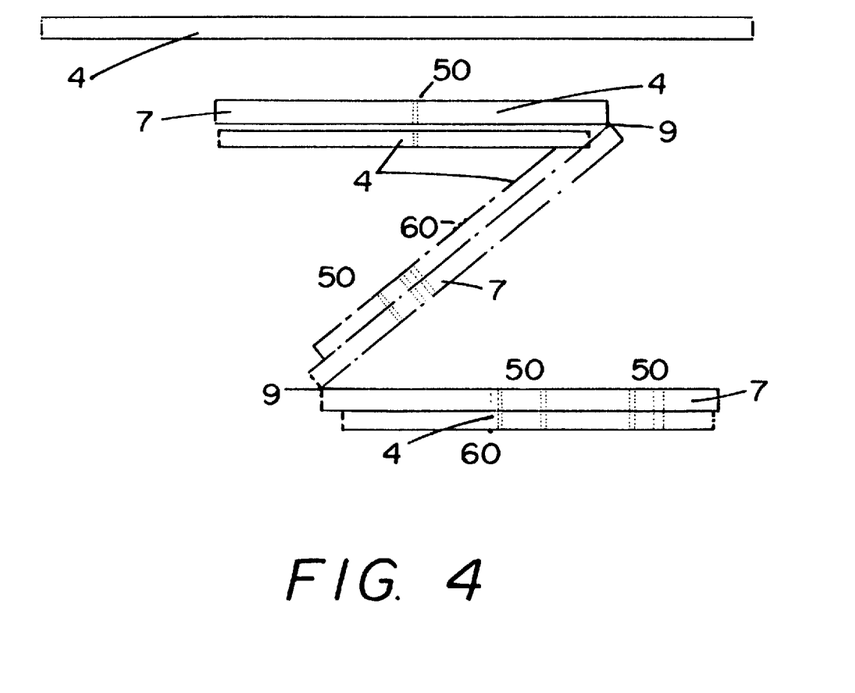
FIG. 4 is a schematic illustration in a side view, of the recording medium shown in FIG. 3, in folded condition; a removable part of this embodiment is shown above the part in folded condition.

FIG. 3 shows another embodiment of a recording medium 1 which comprises a flat rectangular segment, a piece of plastic sheet which by folding along lines 9 is separated into three different parts 7 of definite size. In this case, the plastic sheet is folded on the folding lines, as illustrated in FIG. 4, the three removably fixed and equally-sized parts 7 of the plastic sheet form three layers which are positioned one atop the other in congruence.

Figure 5:
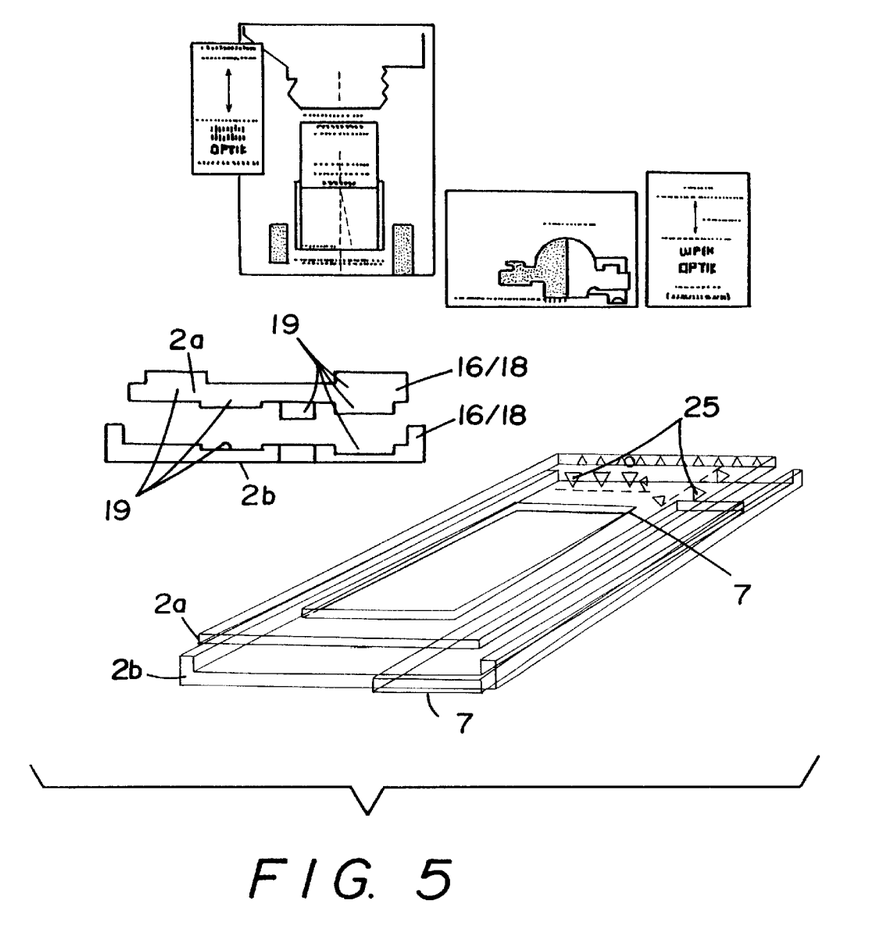
FIG. 5 is a schematic illustration in a perspective view, of an embodiment of the device according to the invention with various accessories.

FIG. 5 shows an embodiment of the invention which comprises a recording medium 1 (as shown in FIG. 1) and a base 2. The base 2 comprises an upper base portion 2a and lower base portion 2b. At least the upper side of the upper base portion 2a is planar and holds a segment 7 of the recording medium 1. The upper and lower base portions 2a, 2b are on their sides facing each other provided with profiles 18 in such a way that the upper base portion 2a is slidably guided on the lower base portion 2b. Furthermore, there is a formal surface structuring. The plate consists of matching form parts. The upper base 2a is fixed on the lower base portion 2b.

Figure 5A:
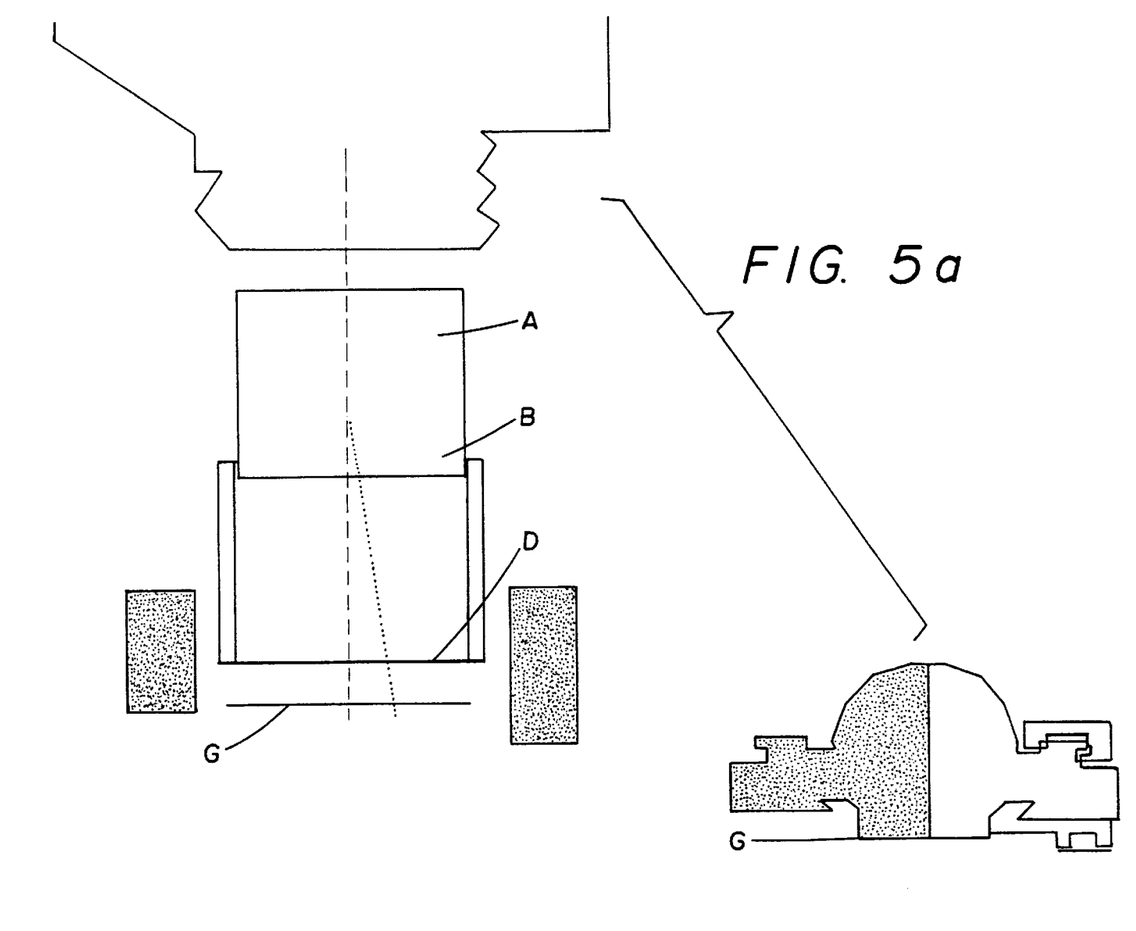
FIG. 5a is a partially enlarged view of the optics mechanisms used in connection with the device shown in FIG. 5.

FIG. 5a shows a scheme of an optical system A-D which may be used in connection with the device G according to the invention as set forth below.

Figure 6:
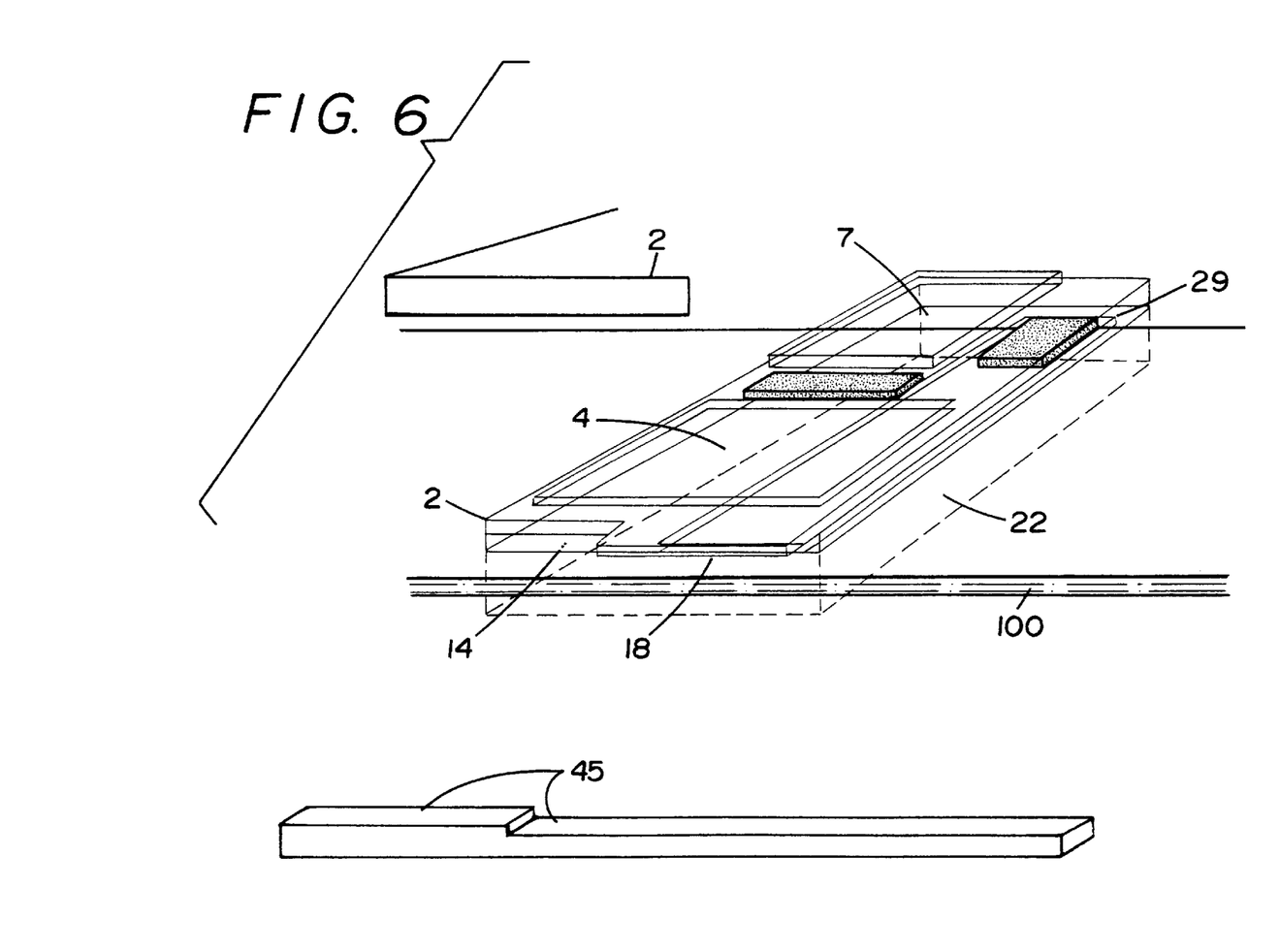
FIG. 6 is a perspective view of another embodiment of the device according to the invention.

FIG. 6 shows another embodiment of the device according to the invention which comprises a planar base 2 on which a recording medium 1, in the form of flat rectangular pieces 7 of transparent material or transparent sheet, are positioned. In this case, the planar base 2 is positioned on a hardcopy (represented by lines 100 in FIG. 6) containing the graphical information to be selected recorded or analyzed.

Figure 7:
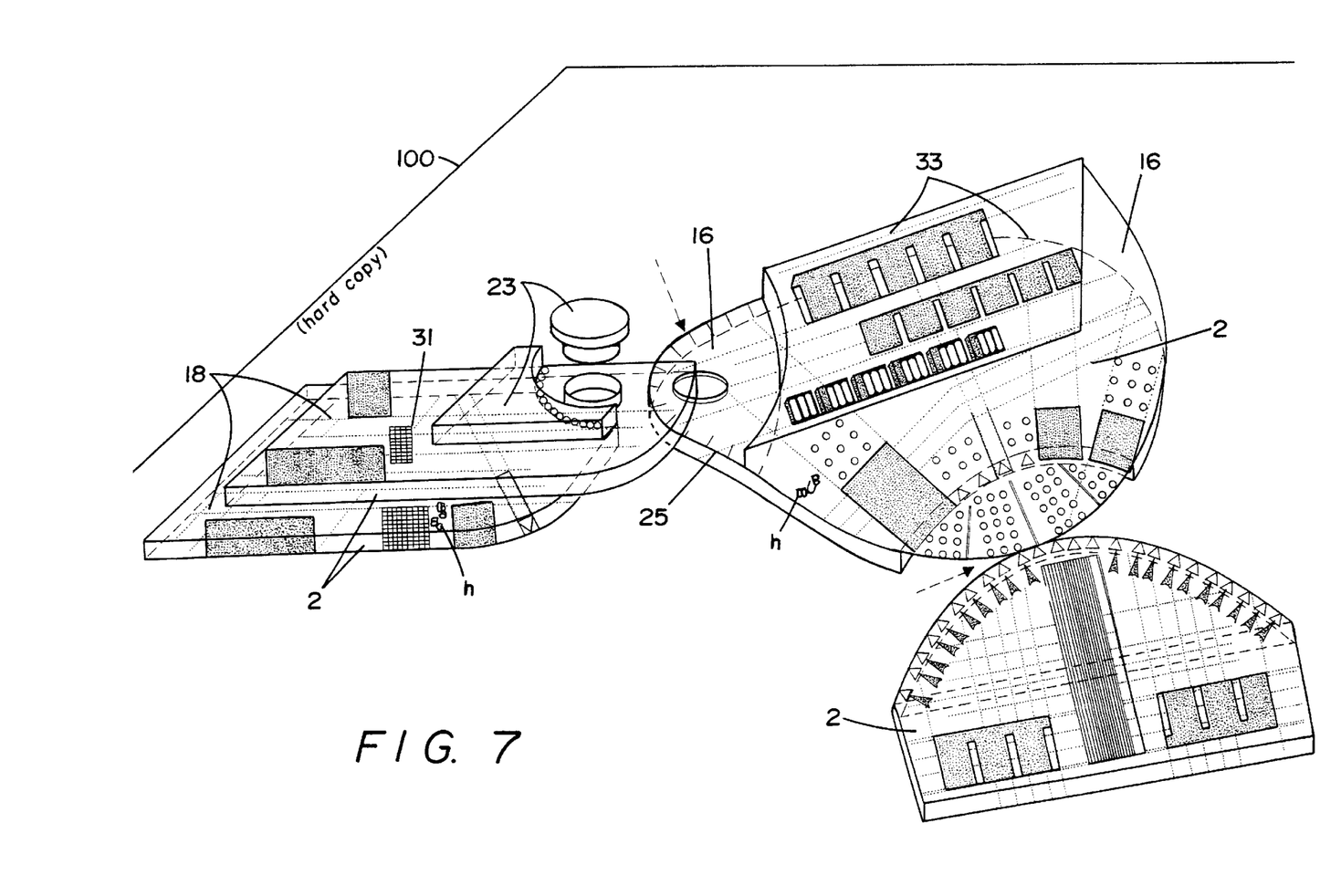
FIG. 7 is a perspective view of another embodiment of the device according to the invention.

FIG. 7 shows another embodiment of the device according to the invention comprising three transparent segments 2 of which two are connected, movable relative to each other and may be clamped in an adjusted position. A third segment, a single—layer plate, is movable relative to the other segments, but cannot be clamped. In this case the three transparent segments overlie a hardcopy 100 which contains the graphical information to be recorded. FIG. 8, 8a–8c show apparatus of the invention.

Figure 9:
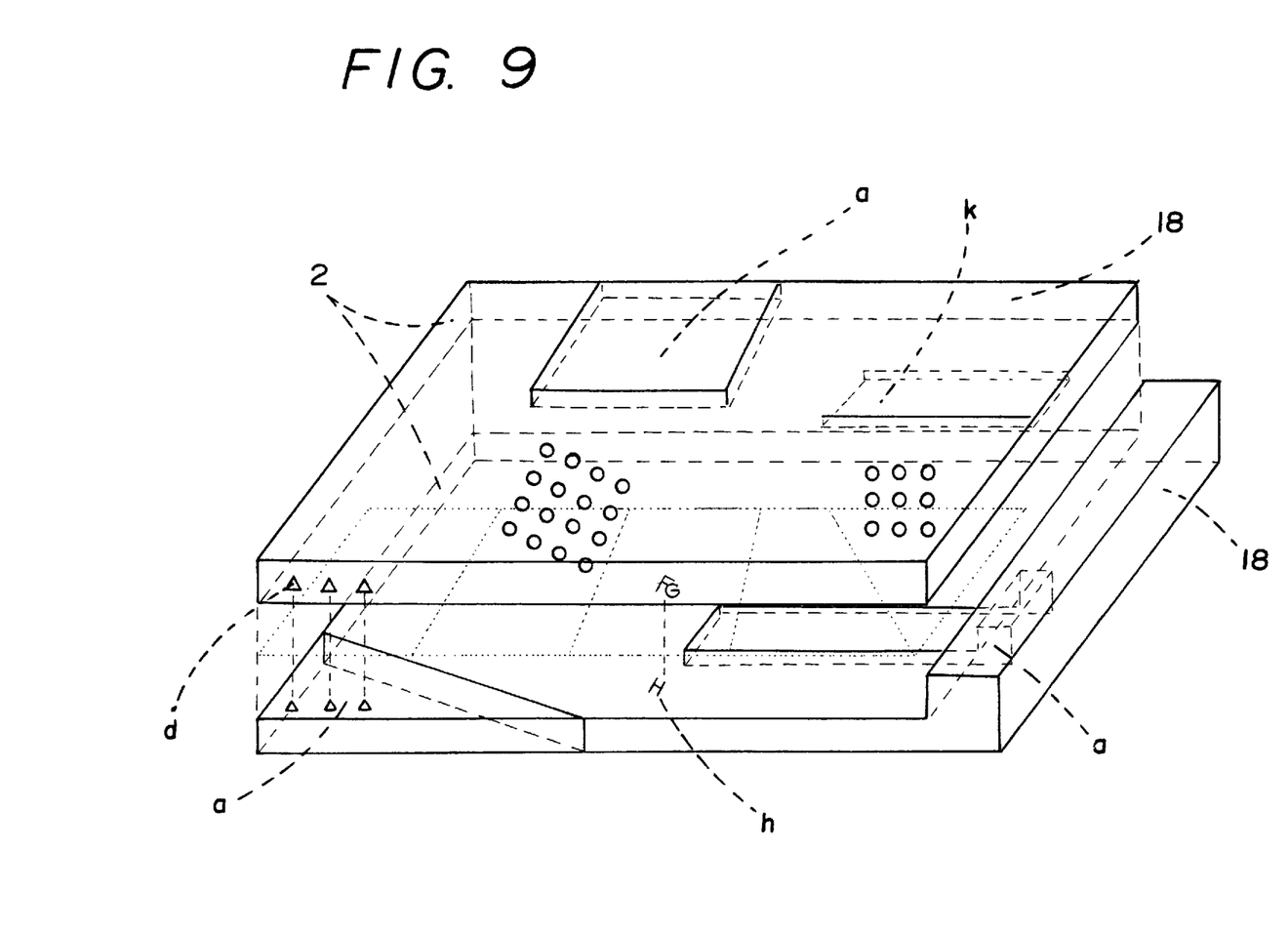
FIG. 9 is a schematic illustration of the cooperation of two transparent segments of the recording device.

FIG. 9 is an illustration of structural components of another embodiment of the device according to the invention.

Figure 10A:
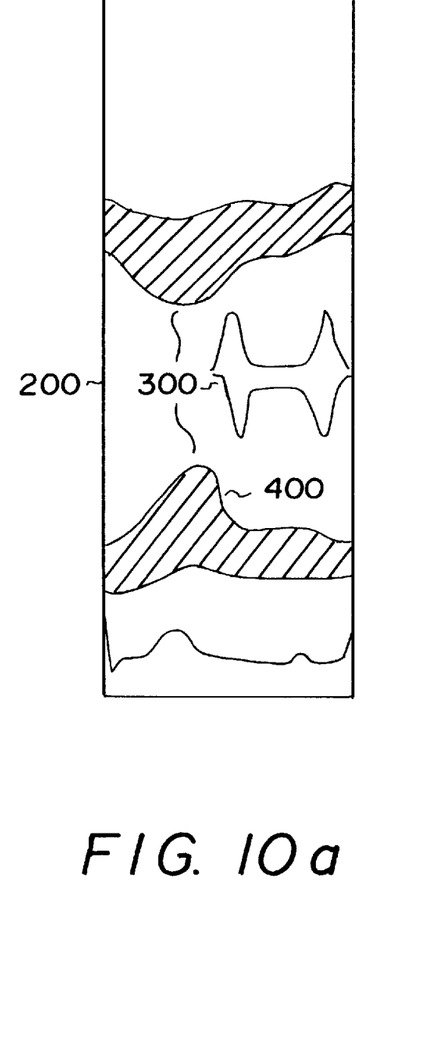
FIGS. 10a, 10b show in a schematic view hardcopies containing curves representing medical data.
Figure 10B:
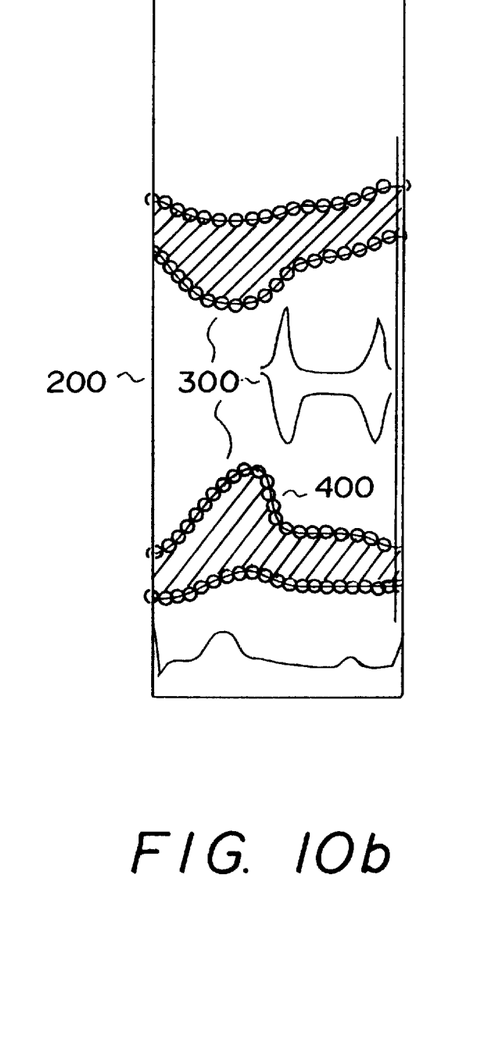

FIG. 10a illustrates a paper strip 200 which contains graphical information in the form of continuous curves 300, representing medical data from an echocardiographic tape or the like. As illustrated in FIG. 10b, curves 300 may be approximated by a series of discrete dot-like picture elements positioned along the curve.

Figure 8:
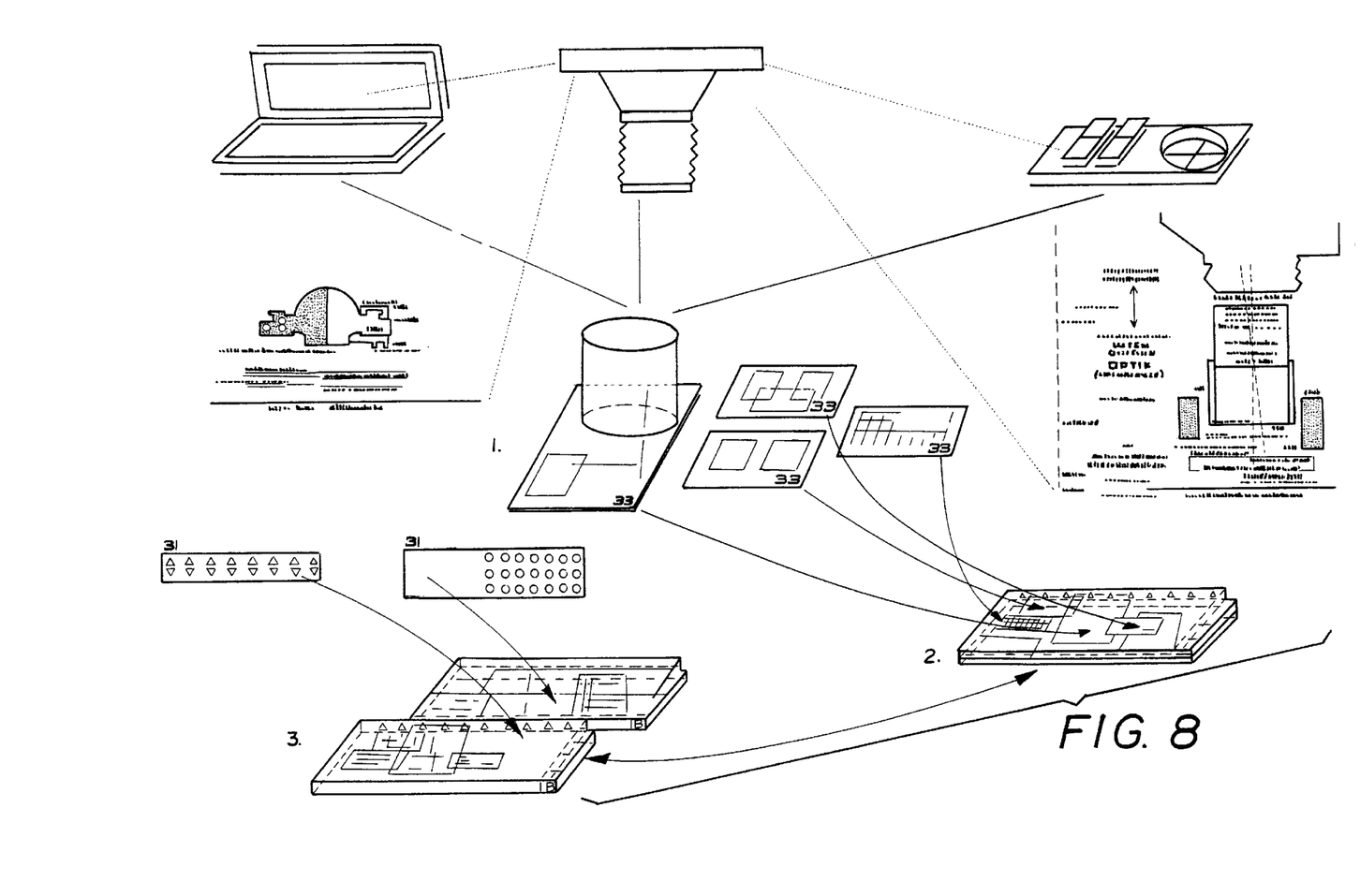
FIGS. 8, 8a–8b schematically illustrate the overall device of the invention.
Figure 8A:
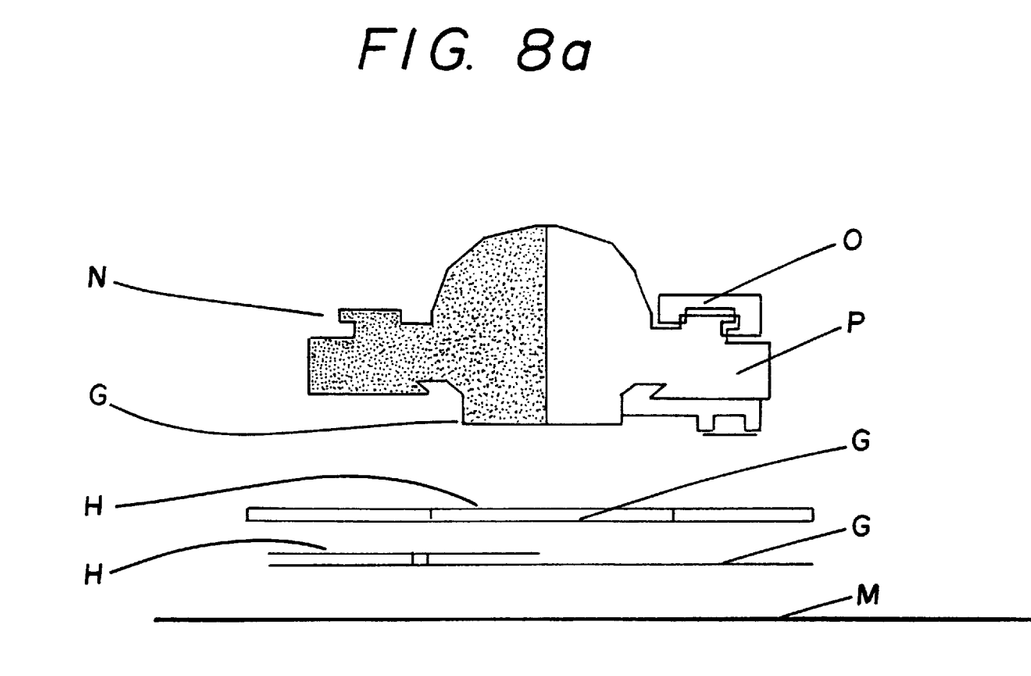
Figure 8B:
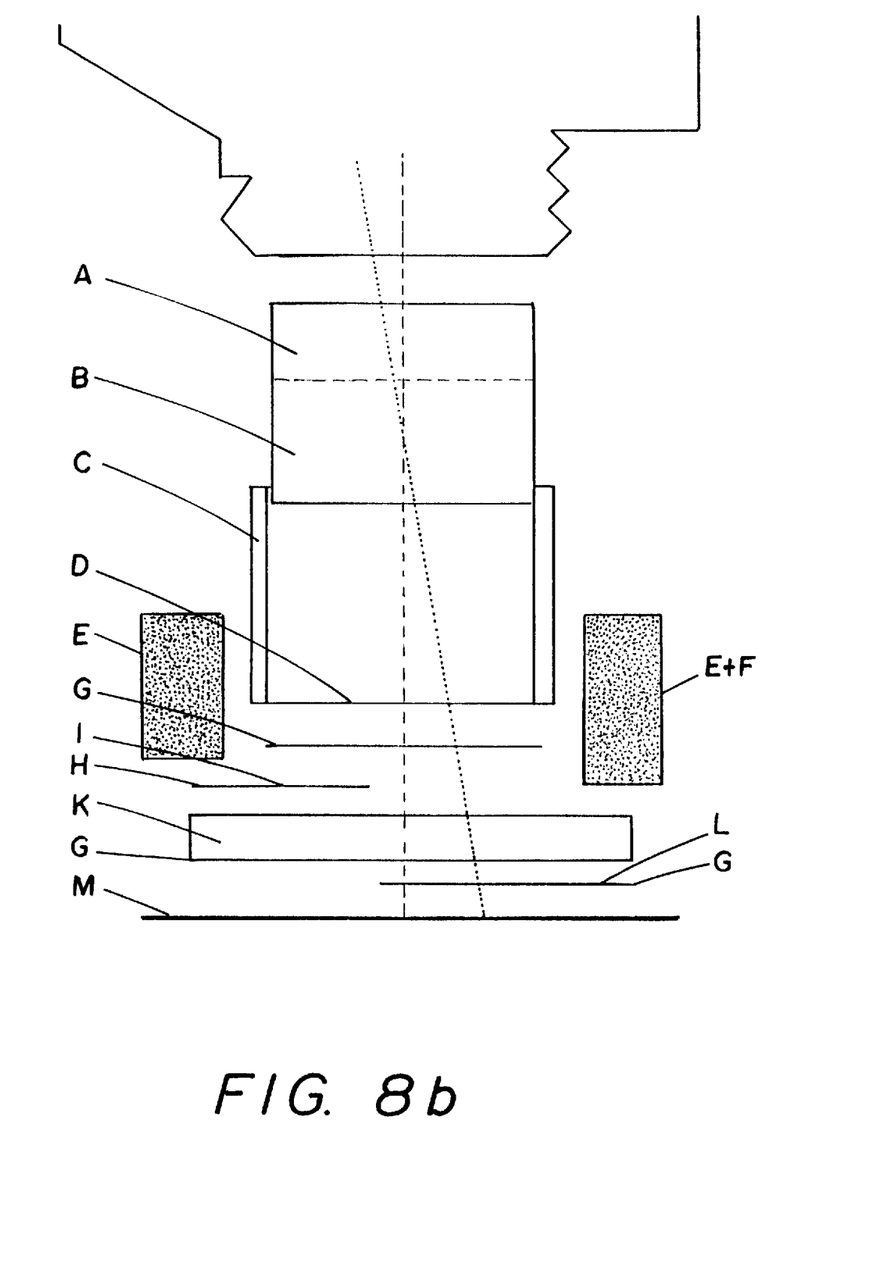
Figure 8C:
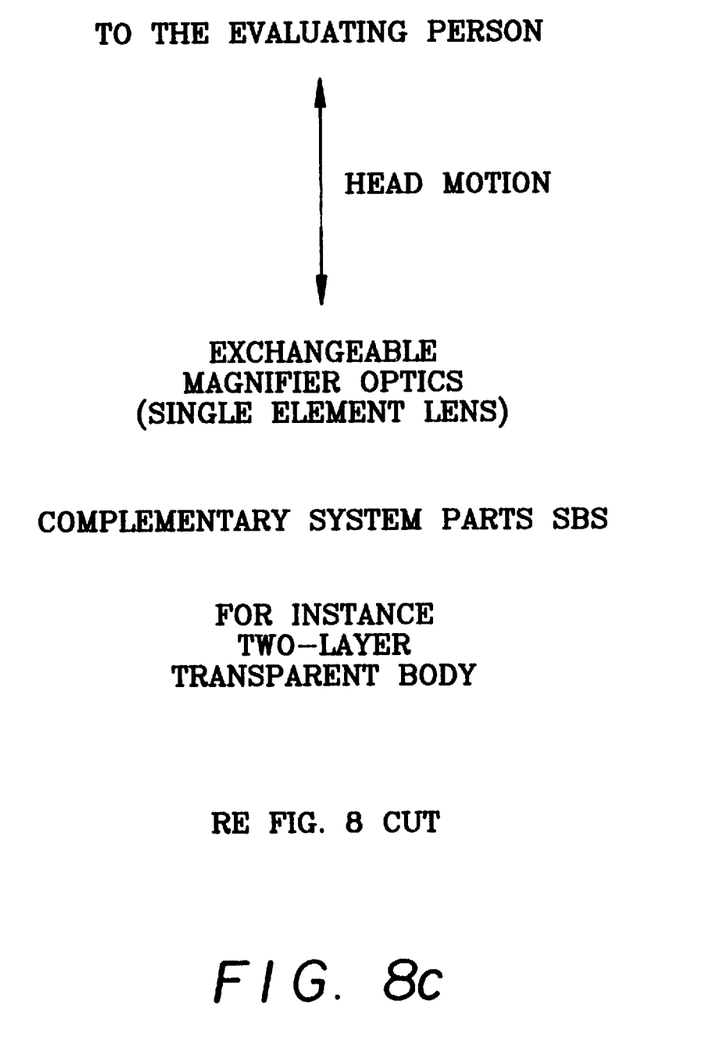
FIG. 8c is a flow chart illustration of the method in using the device of the invention.

The following is a table of items shown in FIGS. 5 and 8.

A photo adapter ring (focusing, exchangeable, at least on lens element)
B photo-adapter ring (a planar, exchangeable, at least two lens elements)
C transparent case
D ocular plate
E annular base segment
F adapter ring segment
G markings (both sides)
H markings (top sides)
I adhesive sheet
K transparent support
L sheet card
M photo (graphic) artwork/hard copy artwork
N connection strip/guide rail/partial system I (applicable to 32/34; 40/42 of partial system I)
O horizontal double rails (segments)/guide ring segment (see 31, 31'; 33, 33'; 22, 24; (303); (304)
P transparent unit The device according to the invention works as follows: First the planar base 2 (see FIG. 6) is positioned upon the hardcopy (see FIG. 10a). Then a recording medium 1, for example the piece of plastic sheet as shown in FIG. 1, is positioned upon the base 2 and removably fixed to the base 2, for example by an adhesive tape or the like. Since the base 2 and the recording medium 1 are transparent, the curves 300 contained on the hardcopy 100 can be inspected through the recording medium 1 and the base 2.

Figure 11:
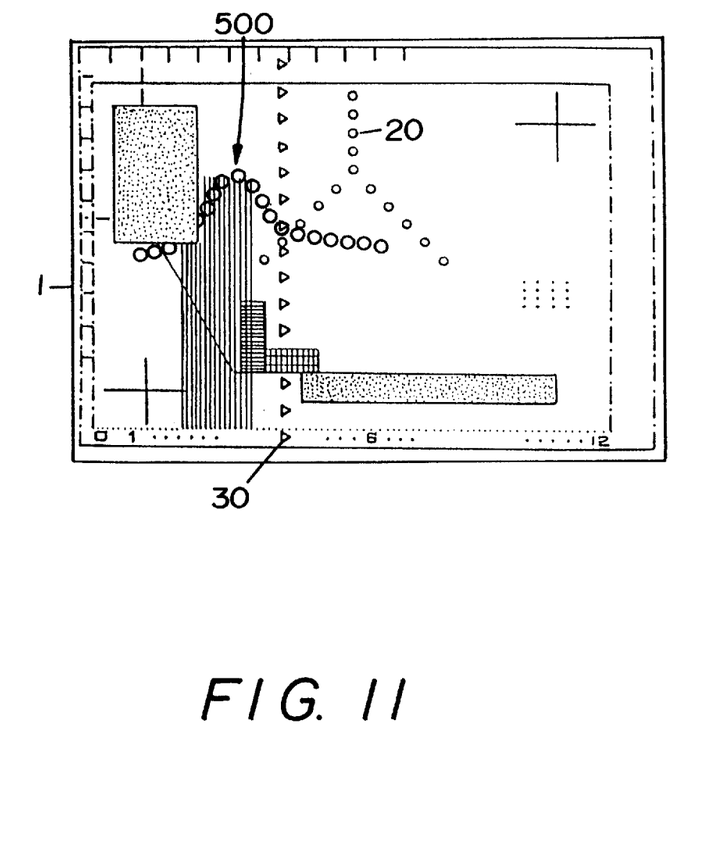
FIG. 11 shows the recording medium of FIG. 1, on which graphical information represented by punch marks is stored.

In order to record a continuous curve (which can be approximated by a series of subsequent discrete dot-like picture elements, see FIG. 10b) the recording medium 1 is marked by a punching means (not illustrated in the figures), at discrete positions along the curve. Since the recording medium 1 is made of flexible material and the base 2 is made of rigid material, only the recording medium 1 is marked. When a whole curve—or part 400 (see FIG. 10a) of the curve as desired—has been recorded to the medium 1 as described above, the recording medium 1 may be removed from the base 2. The recording medium 1 now in form of punch-marks 500 (see FIG. 11) contains an accurate record of the graphical information 400, the graphical information 400 is stored on the recording medium. By means of the elements 20, 30, 40 contained on the recording medium, for example the dot matrix 20, the graphical information stored on the recording means may be analyzed in an easy manner.

With the device according to the invention selection and recording of graphical information can be performed in a quick and easy manner. The recording medium simply may consist of a piece of transparent material. In a simple embodiment it is an inexpensive plastic sheet.

Since the graphical information is stored on a recording medium in the form of a mechanical/optical storage medium, the information, contrary to the information typically stored on a magnetic media—cannot be adversely effected by computer viruses or the like.

If necessary, the graphical information stored on the recording medium, represented by the marks—(punch marks, pencil marks, virtual marks (the graphical information of at least two layers defines temporarily at least one mark) or a selected point of interest. The user can choose between the different ways to mark the graphical information and is further able to mark underlying hardcopies or the like at the selected positions.

It can be preferred that the recording medium is marked by punching since the graphical information represented by the punch marks may be digitized in a quick and easy manner simply by introducing the tip of a digitizer into the punch marks. Accordingly, it is possible to store selected information at least in a single layer comprising at least four equally spaced dot-shaped single markings or sequences of markings which also may be designed in a different formal manner and which are in the form of at least one single matrix 10 or at least a three-path sequence of markings 20.

It is another advantage of the device according to the invention that multiple identical copies of the information recorded to the recording medium may be obtained. This is performed by using a recording medium which may consist of several layers which are placed one upon the other in congruence (see FIG. 3). In this embodiment, several layers of the recording medium are punched simultaneously at identical positions, as illustrated by a punch mark 50 in FIG. 4. In order to improve accuracy in punching the recording medium at the correct positions, an optical system, for example a magnifying glass or transparent plastic segment, may be used for inspecting the hardcopy in a magnified scale.

The recording medium may consist of several segments positioned side by side, or connected to each other side by side which after recording the selected information to the recording medium are separated in such a way that each of the segments contains a part of this information. Therefore, all segments are necessary in order to obtain the complete information stored on the recording means. This may be used as a anti-tampering means, for example by keeping the several separated segments in different places.

A further anti-tampering means may consist of at least a part of the indicia. For example, when the recording medium consists of at least two segments, indicia placed on the respective segments may contain information about the correct orientation of the segments relative to each other. Therefore, a person knowing the meaning of the corresponding indicia can put together the several segments in the correct orientation and therefore only that person knowing the meaning of the indicia may have access to the complete graphical information stored on the recording medium.

The recording medium may be obtained in simple and easy manner by printing or photocopying the indicia as desired on a piece of plastic sheet or plastic foil.

It is also possible to use a base which is not made of a rigid material but is made of a plastic sheet of foil. In this embodiment the recording medium overlying the base, the base overlying a hardcopy, and the hardcopy itself may be punch-marked or simultaneously at identical positions.

Since the recording medium according to the invention is transparent, it allows for comparing graphical information stored on different recording medium by simply placing the respective recording medium one upon the other and comparing the marks, or by marking a single recording medium several times by using the punch marks, by using the punch-marks in combination with a digital and color pencil or by using markings of different colors instead of punch markings.

Some basic features of the invention can be summarized as follows:

1. Simple-structured design consisting of a base and a recording medium, the base and the recording medium being reversibly fixed to each other.
2. As a recording medium, an inexpensive plastic sheet or foil suitable for marking may be used.
3. Simple manufacture of the indicia since very economical and low effort reproduction methods, for example, computer printing, or color laser copying, are available.
4. Selective data processing and transferring of graphical information by means of the indicia deposited on the recording medium.
5. Anti-tampering means: Elements structuring forms and surfaces of the recording medium; markings; indicia, and additionally deposited graphic codes such as symbols, characters and the like.
6. Quick, reproducible, transferring, recording and storage of graphical information in a small space.
7. Easy comparison of graphical information stored on different recording medium.
8. Punch marking: Making identical multiple copies of the graphical information.
9. Color marking of the recording means may be used instead of punch marking.
10. Nearly unlimited and very economical transfer of information.
11. Safety and protection of information stored on the recording means.

OPERATION

In operation, the device of the present invention is positioned on a sample containing the graphical information. Since the device is comprised of transparent material, the graphical information on the sample is visible through the device and can be inspected therethrough. Once the device has been properly aligned on the sample, the recording medium which overlies the base, is marked by a mechanical instrument, such as a pen, or by punching the recording medium with a sharp instrument or the like, essentially to trace the underlying graphing information. In other words, the graphical information is traced onto the recording medium for further analysis and storage purposes. Once the graphical information has been recorded, the recording medium can be separated from the base for further use.

In order to prevent unauthorized access or tampering of the information, the recording medium can be divided into several predefined pieces which are then stored separately from each other. In order to compare and analyze the information recorded on different recoding mediums, the recording mediums can simply be laid one on top of the other and the information thereon compared. If necessary, the information recorded on the recording medium can easily be digitized. For example, a digital pen can be inserted in the punch marks on the recording medium and the series of the marks can be digitized sequentially. As a result, continuous graphical data, for example, curves or the like, are transformed into discrete data since the punch marks or the writing marks represent discrete points or pixels of the continuous graphical data.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as may be applied to the central features hereinbefore set forth, and fall within the scope of the invention and of the limits of the appended claims.

What I claim is:

1. A device for recording from a sample graphical information representing medical data for analysis and storage purposes, comprising:
   a) a generally planar base made of a generally transparent material for overlying a sample containing graphical information representing medical data to be recorded;
   b) means for recording information operably associated with said base;
   c) said information recording means including a generally planar recording medium made of a generally transparent material overlying said base to provide a multilayer structure through which the graphical information on the sample may be readily viewed;
   d) said recording medium adapted to receive thereon indicia corresponding to the graphical information contained on the sample;
   e) said information recording medium comprising a material selected from the group consisting of foil, glass, gelatin and film material; and,
   f) anti-tampering means for preventing unauthorized tampering of information stored on said recording medium.

2. The device of claim 1, wherein:
   a) said information recording medium comprises a plurality of detachably connected segments; and
   b) each said segment generally corresponds in dimension to said base.

3. The device of claim 2, wherein:
   a) said segments are each made of a different material.

4. The device of claim 1, wherein:
   a ) said generally planar recording medium comprises at least two layers overlying each other.

5. The device of claim 1, wherein:
   a) said information recording medium is made of a material that can be marked by using a mechanical means.

6. The device of claim 1, wherein:
   a) said indicia comprises a dot matrix.

7. The device of claim 1, wherein:
   a ) said indicia comprises a generally triangularly shaped matrix.

8. The device of claim 1, wherein:
   a) said indicia comprises at least one block-sequence of marks or signs.

9. The device of claim 1, wherein:
   a) at least a part of said base is made of a rigid material.

10. A device for recording from a sample graphical information representing medical data for analysis and storage purposes comprising:
    a) a generally planar base made of a generally transparent material for overlying a sample containing graphical information representing medical data to be recorded;
    b) means for recording information operably associated with said base;
    c) said information recording means including a generally planar recording medium made of a generally transparent material overlying said base to provide a multilayer structure through which the graphical information on the sample may be readily viewed;
    d) said recording medium adapted to receive thereon indicia corresponding to the graphical information contained on the sample;
    e) said information recording medium comprising a material selected from the group consisting of foil, glass, gelatin and film material;
    f) anti-tampering means for preventing unauthorized tampering of information stored on said recording medium; and,
    g) said anti-tampering means comprising a plurality of detachably connected recording mediums.

11. A method of recording graphical information representing medical data for analysis and storage purposes from a sample, comprising the steps of:
    a) placing a generally planar base made of a generally transparent material on a sample containing the graphical information representing medical data to be recorded;
    b) placing a recording means on said base, said recording means comprising a generally planar recording medium made of a generally transparent material overlying said base to provide a multilayer structure through which the graphical information on the sample may be readily viewed;
    c) immobilizing said recording means on said base;
    d) inspecting the graphical information on the sample through said base and said recording means and marking said recording medium by using a punching means so as to place dot-like punch marks thereon at locations corresponding to the graphical information, each of said dot-like punch marks representing a dot element of the graphical information on the sample;
    e) said recording medium comprises a material selected from the group consisting of foil, glass, gelatin, and film material; and,
    f) said recording means further comprising anti-tampering means for preventing unauthorized tampering of information stored on said recording medium.

12. The method of claim 11, wherein:
a) said recording medium comprises at least two layers of transparent material, said layers overlying each other and are marked simultaneously by punching.

13. The method of claim 11, wherein:
a) said base and said recording mean s are detachably connected.

14. The method of claim 11, further including the step of:
a) illuminating said base and said recording means using a light source.

15. The method of claim 11, where:
a) said recording medium includes indicia for analyzing the graphical information on the sample.

* * * * *